US012690767B2

(12) United States Patent
Shang et al.

(10) Patent No.: US 12,690,767 B2
(45) Date of Patent: Jul. 28, 2026

(54) EYE TRACKING METHOD AND APPARATUS FOR ANTERIOR SEGMENT OCTA, DEVICE, AND STORAGE MEDIUM

(71) Applicant: TOWARDPI (BEIJING) MEDICAL TECHNOLOGY LTD., Beijing (CN)

(72) Inventors: Xuesen Shang, Beijing (CN); Xiao Wang, Beijing (CN)

(73) Assignee: Towardpi (Beijing) Medical Technology, LTD., Beijing (CN)

( * ) Notice: Subject to any disclaimer, the term of this patent is extended or adjusted under 35 U.S.C. 154(b) by 280 days.

(21) Appl. No.: 18/717,705

(22) PCT Filed: Oct. 21, 2022

(86) PCT No.: PCT/CN2022/126616
§ 371 (c)(1),
(2) Date: Jun. 7, 2024

(87) PCT Pub. No.: WO2023/103609
PCT Pub. Date: Jun. 15, 2023

(65) Prior Publication Data
US 2025/0057413 A1      Feb. 20, 2025

(30) Foreign Application Priority Data

Dec. 7, 2021    (CN) .......................... 202111489187.2

(51) Int. Cl.
A61B 3/10      (2006.01)
A61B 3/00      (2006.01)
(Continued)

(52) U.S. Cl.
CPC ............ A61B 3/102 (2013.01); A61B 3/0025 (2013.01); G06T 7/0014 (2013.01); G06T 7/168 (2017.01);
(Continued)

(58) Field of Classification Search
CPC ....... A61B 3/102; A61B 3/0025; A61B 3/113; G06T 7/62; G06T 7/168; G06T 7/66;
(Continued)

(56) References Cited

U.S. PATENT DOCUMENTS

| 5,982,374 A | 11/1999 | Wahl | |
| 2020/0237209 A1* | 7/2020 | Clifton | ................. A61B 3/0025 |
| 2022/0301284 A1* | 9/2022 | Li | ........................ G06V 10/757 |

FOREIGN PATENT DOCUMENTS

| CN | 101458766 A | 6/2009 |
| CN | 104545788 A | 4/2015 |

(Continued)

OTHER PUBLICATIONS

Takumichi Sugawara: Notice of Reasons for Refusal for JP App. No. 2024-534540; May 7, 2025; 8 pages; Japanese Patent Office, JP.

(Continued)

*Primary Examiner* — Stephone B Allen
*Assistant Examiner* — Boutsikaris Leonidas
(74) *Attorney, Agent, or Firm* — Crain Caton & James, P.C.; William P. Jensen

(57) ABSTRACT

Provided are an eye tracking method and apparatus for anterior segment OCTA, a device, and a storage medium. The eye tracking method for anterior segment OCTA includes: acquiring two consecutive frames of pupil images; separately performing contour extraction on the two frames of pupil images to obtain two corresponding pupil contours; determining whether the two pupil contours are similar to a reference contour, and in response to the two pupil contours being similar to the reference contour, calculating a central position offset of one of the two pupil contours with respect to the other pupil contour.

18 Claims, 4 Drawing Sheets

(51) Int. Cl.
  *G06T 7/00*      (2017.01)
  *G06T 7/168*     (2017.01)
  *G06T 7/62*      (2017.01)
  *G06T 7/66*      (2017.01)

(52) U.S. Cl.
  CPC .................. *G06T 7/62* (2017.01); *G06T 7/66*
      (2017.01); *G06T 2207/20048* (2013.01); *G06T*
      *2207/30041* (2013.01)

(58) Field of Classification Search
  CPC ......... G06T 7/0014; G06T 2207/20048; G06T
                                        2207/30041
  USPC ........................................................ 351/206
  See application file for complete search history.

(56)                References Cited

FOREIGN PATENT DOCUMENTS

| CN | 105095840 A | | 11/2015 | |
|----|-------------|---|---------|---|
| CN | 106791353 A | | 5/2017 | |
| CN | 107767392 A | | 3/2018 | |
| CN | 107875526 A | | 4/2018 | |
| CN | 109389622 A | | 2/2019 | |
| CN | 109664891 A | | 4/2019 | |
| CN | 109977833 A | | 7/2019 | |
| CN | 110807427 A | * | 2/2020 | ............. G06F 18/22 |
| CN | 111148460 A | * | 5/2020 | ........... A61B 3/0025 |
| CN | 112732071 A | | 4/2021 | |
| CN | 112883767 A | | 6/2021 | |
| CN | 112991394 A | | 6/2021 | |
| CN | 113040701 A | | 6/2021 | |
| CN | 113129334 A | | 7/2021 | |
| CN | 113164036 A | | 7/2021 | |
| CN | 113348487 A | | 9/2021 | |
| CN | 114373216 A | | 4/2022 | |
| JP | H08504979 A | | 5/1996 | |
| JP | 2016024616 | | 2/2016 | |
| JP | 2016024616 A | * | 2/2016 | |
| JP | 2016140406 | | 8/2016 | |
| JP | 2018029764 A | | 3/2018 | |
| JP | 2018531773 | | 11/2018 | |
| JP | 2020128945 A | | 8/2020 | |
| JP | 2020530632 A | | 10/2020 | |
| JP | 2021000259 A | | 1/2021 | |
| JP | 2021144371 A | | 9/2021 | |
| JP | 2021532405 A | | 11/2021 | |
| WO | 2017218738 A1 | | 12/2017 | |
| WO | WO-2021219773 A1 | * | 11/2021 | ........... A61B 3/0025 |

OTHER PUBLICATIONS

Jyoti Paul, Examination Report No. 1 for AU App. No. 2022406948, Jun. 27, 2025, 6 pages, IP Australia.

Carrasco et al., 'Pupil tracking optical coherence tomography for precise control of pupil entry position', Biomedical optics express. Aug. 17, 2015, 6(9), pp. 3405-3419, DOI: 10.1364/BOE.6.003405, <URL: https://pmc.ncbi.nlm.nih.gov/articles/PMC4574666/>, [retrieved on Jun. 27, 2025].

Bozomitu et al., 'Pupil centre coordinates detection using the circular Hough transform technique', In2015 38th International Spring Seminar on Electronics Technology (ISSE), May 6, 2015, pp. 462-465, IEEE, DOI: 10.1109/ISSE.2015.7248041, <URL: https://ieeexplore.ieee.org/document/7248041>, [retrieved on Jun. 27, 2025].

Xu Xiaoyan, International Search Report for PCT Application No. PCT/CN2022/126616; 4 pages; China National Intellectual Property Administration as the International Search Authority; Beijing, CN.

Tongfeng Cui, et al.; Application of Optical Coherence Tomography Angiography in Ocular Anterior Segment Diseases; Journal of Ophthalmology; vol. 36, No. 7; Jul. 2021; 4 pages.

I. A. Matveev; Circular Shortest Path as a Method of Detection and Refinement of Iris Borders in Eye Image; Journal of Computer and Systems Sciences International; Oct. 2011; 12 pages.

Jiahui Wu, et al.; Reduced Macular Vessel Density and Capillary Perfusion in Glaucoma Detected Using OCT Angiography; Current Eye Research; Dec. 21, 2018; 22 pages.

Meng Huanyu; First Office Action for CN App. No. 202111489187. 2; Aug. 19, 2022; 16 pages; State Intellectual Property Office; Beijing, China.

Meng Huanyu; Second Office Action for CN App. No. 202111489187. 2; Dec. 27, 2022; 14 pages; State Intellectual Property Office; Beijing, China.

Meng Huanyu; Notice of Rejection for CN App. No. 202111489187. 2; Apr. 28, 2023; 20 pages; State Intellectual Property Office; Beijing, China.

Meng Huanyu; Third Office Action for CN App. No. 202111489187. 2; Dec. 28, 2023 20 pages; State Intellectual Property Office; Beijing, China.

Giovanni Tommaseo; European Search Report for EP App. No. 22903033.3; Nov. 13, 2025; 10 pages; European Patent Office; Munich, Germany.

\* cited by examiner

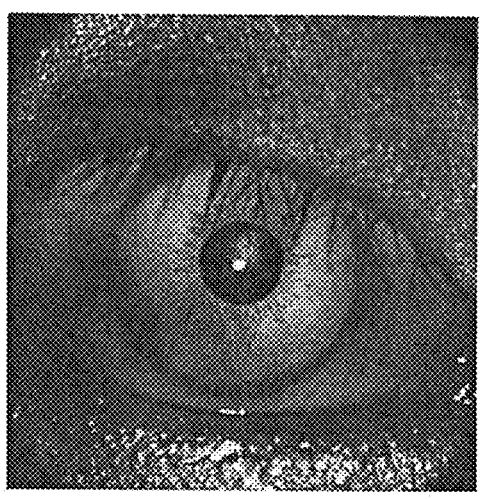

FIG. 1

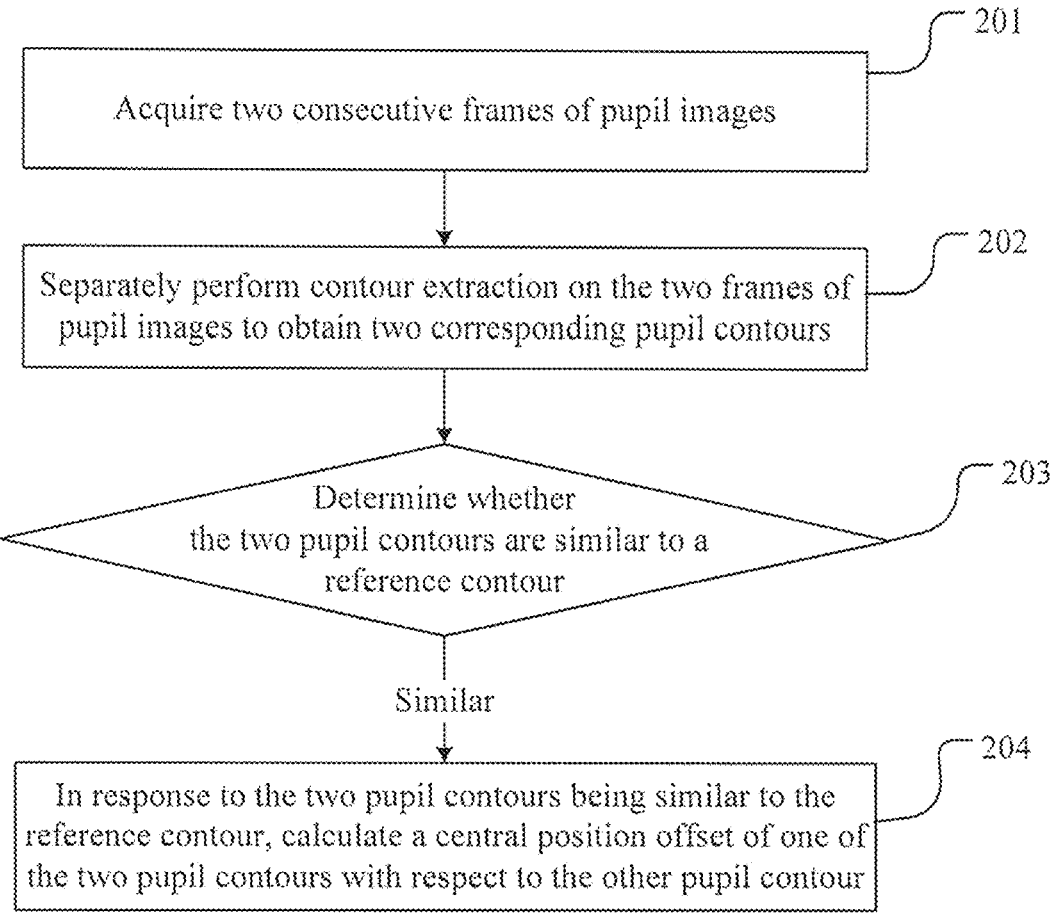

Acquire two consecutive frames of pupil images                    201

Separately perform contour extraction on the two frames of
pupil images to obtain two corresponding pupil contours          202

Determine whether
the two pupil contours are similar to a
reference contour                                                203

Similar

In response to the two pupil contours being similar to the
reference contour, calculate a central position offset of one of
the two pupil contours with respect to the other pupil contour   204

FIG. 2

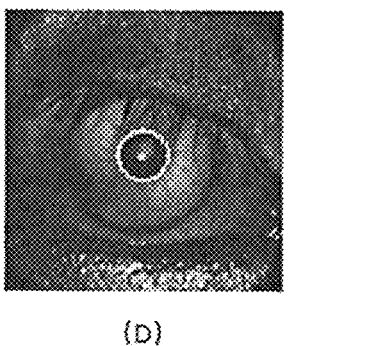
(D)
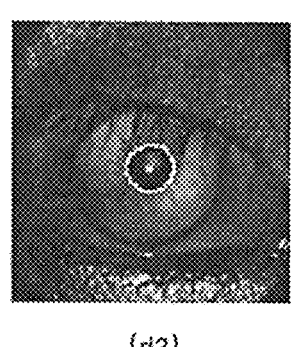
(d3)
FIG. 5
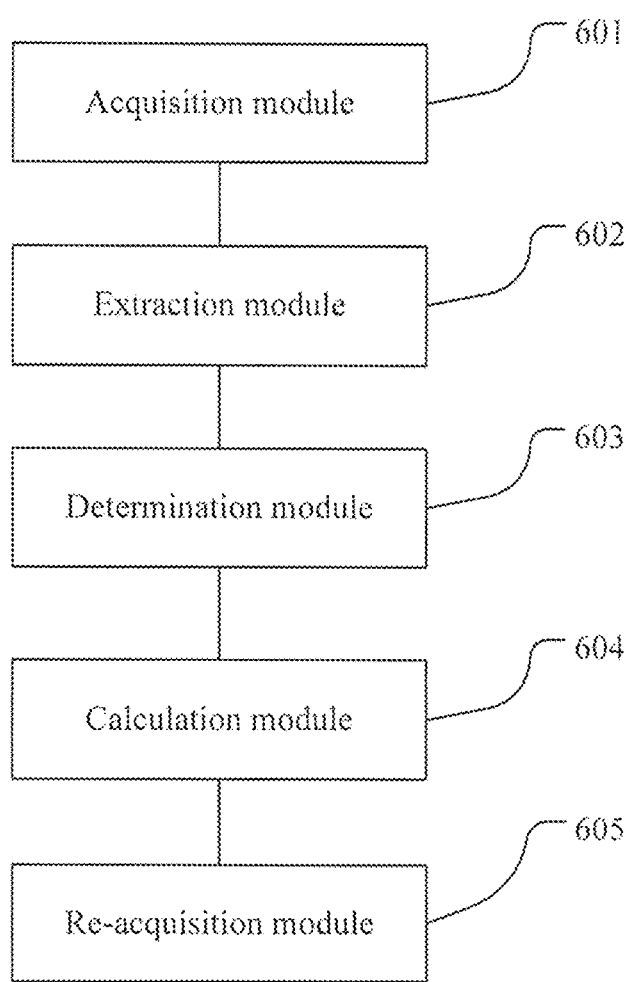
FIG. 6

EYE TRACKING METHOD AND APPARATUS FOR ANTERIOR SEGMENT OCTA, DEVICE, AND STORAGE MEDIUM

CROSS-REFERENCES TO RELATED APPLICATIONS

This application is a national stage application filed under 35 U.S.C. 371 based on International Patent Application No. PCT/CN2022/126616, filed on Oct. 21, 2022, which claims priority to Chinese Patent Application No. 202111489187.2 filed with the China National Intellectual Property Administration (CNIPA) on Dec. 7, 2021, the disclosure of which is incorporated herein by reference in its entirety.

TECHNICAL FIELD

The present disclosure relates to the field of eye tracking, for example, to an eye tracking method and apparatus for anterior segment optical coherence tomography angiography (OCTA), a device, and a storage medium.

BACKGROUND

OCTA, originally applied to the posterior segment of the eye, that is, the fundus, is a new non-invasive fundus imaging technique for high-resolution identification of blood flow movement information of retina and choroid and imaging of retinal-choroidal microvascular circulation in living tissue. OCTA has unique advantages in terms of management follow-up and treatment effect detection of normal retinal-choroidal vascular changes and diseases. In the anterior segment, a blood flow signal of a scanned region is obtained through an optical coherence tomography (OCT) signal change in multiple scans of the same cross-section, and an OCTA image of the scanned region of the anterior segment can be obtained by continuously scanning multiple cross-sections.

The existing OCTA is not suitable for all patients, and when a patient has poor fixation, frequently blinks or moves eyeballs, the OCTA image may become inaccurate.

SUMMARY

The present disclosure provides an eye tracking method and apparatus for anterior segment OCTA, a device, and a storage medium, thereby solving the problems that OCTA is not suitable for all patients and the OCTA image is inaccurate when a patient has poor fixation, frequently blinks or moves eyeballs.

In a first aspect of the present disclosure, an eye tracking method for anterior segment OCTA is provided. The method includes the following steps.

Two consecutive frames of pupil images are acquired.

Contour extraction is performed on the two frames of pupil images separately to obtain two corresponding pupil contours.

Whether the two pupil contours are similar to a reference contour is determined.

In response to the two pupil contours being similar to the reference contour, a central position offset of one of the two pupil contours with respect to the other pupil contour is calculated.

In a second aspect of the present disclosure, an eye tracking apparatus for anterior segment OCTA is provided. The apparatus includes an acquisition module, an extraction module, a determination module and a calculation module.

The acquisition module is configured to acquire two consecutive frames of pupil images.

The extraction module is configured to separately perform contour extraction on the two frames of pupil images to obtain two corresponding pupil contours.

The determination module is configured to determine whether the two pupil contours are similar to a reference contour.

The calculation module is configured to, in response to the two pupil contours being similar to the reference contour, calculate a central position offset of one of the two pupil contours with respect to the other pupil contour.

In a third aspect of the present disclosure, an electronic device is provided. The electronic device includes a memory and a processor. The memory is configured to store a computer program. The processor is configured to, when executing the computer program, implement the eye tracking method for anterior segment OCTA in the embodiments of the present disclosure.

In a fourth aspect of the present disclosure, a computer-readable storage medium is provided. The computer-readable storage medium is configured to store a computer program. The computer program, when executed by a processor, implements the eye tracking method for anterior segment OCTA in the embodiments of the present disclosure.

BRIEF DESCRIPTION OF DRAWINGS

FIG. 1 is a pupil image normally captured according to the present disclosure embodiment;

FIG. 2 is a flowchart of an eye tracking method for anterior segment OCTA according to an embodiment of the present disclosure;

FIG. 5 is a schematic diagram in which a pupil contour is similar to a reference contour according to an embodiment of the present disclosure;

FIG. 6 is a structure diagram of an eye tracking apparatus for anterior segment OCTA according to an embodiment of the present disclosure.

DETAILED DESCRIPTION

Figure 3:
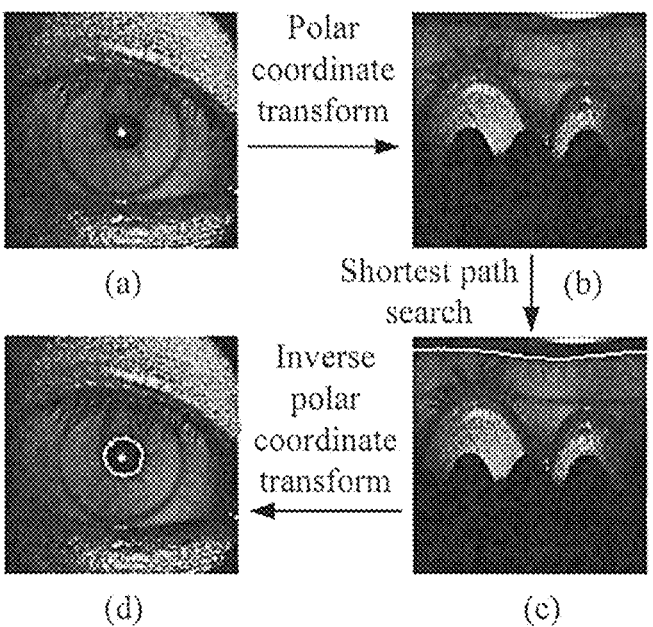
FIG. 3 is a schematic diagram of a pupil contour extraction process according to an embodiment of the present disclosure.

The solutions in embodiments of the present disclosure will be described below in conjunction with drawings in the embodiments of the present disclosure.

The eye tracking method for anterior segment OCTA provided by the embodiments of the present disclosure can be applied to the field of eye tracking.

OCTA is used for detecting the movement of red blood cells in the vessel lumen by measuring the change in the OCT signal obtained from multiple scans of the same cross-section, and after merging the information of consecutive cross-sectional (en face) OCT images, a complete three-dimensional retinal-choroidal vascular image is obtained. The en face OCT is a transverse tomography technique on the basis of conventional high-density B-scan images and by means of software operation processing.

OCTA is not suitable for all patients, and OCTA images with good blood flow continuity and high-quality scan signals can only be obtained in the case where the patient has good fixation and clear dioptric media. The time required for a single OCTA blood flow imaging scan depends on a scan range and a light source frequency. When the scan range is larger and the requirement for the light source frequency is higher, the OCTA imaging time will become longer, and as a result, the patient may have poor fixation, frequently blink or move eyeballs, thereby resulting in poor OCTA scan signal strength and poor image quality.

Therefore, it is necessary to introduce eye tracking during the scan process. With the introduction of eye tracking, automatic positioning and identification of the pupil of a patient and exclusion of the cases of eye blinking and eyeball movement can be achieved to obtain the movement direction and magnitude between two high-quality pupil images at two consecutive positions, thereby enabling the subsequent OCTA imaging to be more accurate.

FIG. 1 is a pupil image normally captured according to the present disclosure embodiment. With reference to FIG. 1, in the related art, the general strategy for identifying a pupil includes steps such as image filtering, image binarization, edge detection and ellipse fitting. In the case of eye blinking, that is, when part or all of a pupil is obscured by the eyelid or eyelashes, the obscured part is generally excluded, and only the effective region is used for ellipse fitting.

As for the process of ellipse fitting, a region of interest is first extracted from an image through a mask, then the image is binarized using a threshold which is obtained through a histogram, a contour is extracted from the binarized image using an edge following algorithm, and finally, ellipse fitting is performed on the extracted contour. If the error between the fitted ellipse and the original contour is greater than a threshold, the outliers are discarded using a random sample consensus algorithm.

As far as the related art is concerned, most schemes require image binarization, but the threshold required for binarization is difficult to determine. Once the image quality is poor or a poor threshold is selected, the region identified by the binarized image may not be the pupil.

In addition, in most schemes, the position of the pupil is identified through ellipse fitting. However, the above identification has multiple disadvantages. For example, in eye examinations, in the case where the pupil of a patient may have been deformed, a large error will be caused when the fitting is still performed with a preset shape such as an ellipse. Furthermore, ellipse fitting itself also introduces errors.

There is no eye tracking scheme specifically for anterior segment OCTA. Whether a patient blinks is also required to be identified in such a customized scheme, which is not involved in most schemes.

To solve the above problems, the embodiments of the present disclosure provide an eye tracking method for anterior segment OCTA. In some embodiments, the eye tracking method for anterior segment OCTA may be executed by an electronic device.

FIG. 2 is a flowchart of an eye tracking method for anterior segment OCTA according to an embodiment of the present disclosure. With reference to FIG. 2, the eye tracking method for anterior segment OCTA in the embodiment includes Operations 201 to 204.

In Operation 201, two consecutive frames of pupil images are acquired.

In the embodiment of the present disclosure, the two consecutive frames of pupil images are two consecutive frames of pupil images arbitrarily selected from normally captured pupil images when OCTA image identification is performed on a patient. The two consecutive frames of pupil images may be acquired by a device that performs diagnostic imaging according to an optical principle.

In the embodiment of the present disclosure, the number of frames of images acquired is determined according to the resolution of the device for performing diagnostic imaging according to an optical principle, and generally, the number of frames of images acquired in one second is 30 frames, 60 frames or 120 frames. The device for performing diagnostic imaging according to an optical principle may generally acquire multiple frames of images over a period of time.

In the embodiment of the present disclosure, the device that performs diagnostic imaging according to an optical principle includes an OCT imaging device and a pupil camera imaging device.

For the convenience of the description of the eye tracking method for anterior segment OCTA, any one group of two consecutive frames of pupil images among the groups of two consecutive frames of pupil images in multiple frames of images are selected as the two consecutive frames of pupil images in specific embodiments and then used for description.

In the embodiment of the present disclosure, the two consecutive frames of pupil images are used for subsequent contour extraction to improve the accuracy of determining whether the patient blinks.

In Operation 202, contour extraction is performed on the two frames of pupil images separately to obtain two corresponding pupil contours.

In the embodiment of the present disclosure, contour extraction is performed on the pupils in the two frames of pupil images separately through polar coordinate transform and a shortest path algorithm to obtain two pupil contours.

FIG. 3 is a schematic diagram of a pupil contour extraction process according to an embodiment of the present disclosure. With reference to FIG. 3, the manner of performing contour extraction on one of the two frames of pupil images is as follows: polar coordinate transform is performed on a normally captured pupil image (a) to obtain a transformed pupil image (b); a boundary of the pupil in the transformed pupil image (b) is extracted based on a shortest path algorithm to obtain a pupil image (c) with the boundary extracted; inverse polar coordinate transform is performed on the boundary in the pupil image (c) with the boundary extracted to obtain a pupil image (d) including a pupil contour.

The pupil contour shown in the pupil image (d) including a pupil contour is a closed-loop contour in the pupil which is at a certain distance from the center of the image.

In the embodiment of the present disclosure, the contour extraction is performed on the pupil in each of the two frames of pupil images separately through the polar coordinate transform and the shortest path algorithm, thereby avoiding the problem in the related art that the region identified by the binarized image may not be the pupil due to the fact that the threshold required for binarization is difficult to determine in the case where the method of image binarization is adopted.

In some embodiments, the contour extraction performed on one frame of pupil image in Operation 202 includes Operations A1 to A3.

In Operation A1, polar coordinate transform is performed on the pupil image to obtain a transformed pupil image.

In Operation A2, a boundary of a pupil in the transformed pupil image is extracted based on a shortest path algorithm.

In Operation A3, inverse polar coordinate transform is performed on the boundary to obtain a pupil contour.

In the embodiment of the present disclosure, the manner of performing contour extraction on one frame of pupil image will be described below.

In the embodiment of the present disclosure, the polar coordinate transform is used for detecting a closed contour in an image. With reference to FIG. 3, a Cartesian coordinate system xoy is established in a pupil image, and the center $(x_0, y_0)$ of the image is generally selected as the transform center. With $(x_0, y_0)$ as the center, any point $(x, y)$ in the plane of the Cartesian coordinate system xoy corresponds to polar coordinates $(\theta, r)$ in a polar coordinate system through the following formula:

$$r = \sqrt{(x - x_0)^2 + (y - y_0)^2}$$

$$\theta = \begin{cases} 2\pi + \arctan2(y - y_0, x - x_0), & y - y_0 \leq 0 \\ \arctan2(y - y_0, x - x_0), & y - y_0 > 0 \end{cases}.$$

FIG. 3 illustrates the process of transforming the normally captured pupil image (a) into the transformed pupil image (b).

In some embodiments of the present disclosure, the pupil boundary under the polar coordinates is found based on a shortest path algorithm. The shortest path algorithm includes the depth-first or breadth-first search algorithm, Floyd's algorithm, Dijkstra's algorithm and the Bellman-Ford algorithm.

In one embodiment, the pupil boundary in the polar coordinates is found based on Dijkstra's algorithm. The operations of finding the pupil boundary in the polar coordinates based on Dijkstra's algorithm are as follows.

In Operation 1, an array N and two sets P and Q are maintained in the transformed pupil image. The array N is used for storing the shortest distance from a starting point to each vertex, the set P is used for storing untraversed points, and the set Q is used for storing traversed points.

In Operation 2, a starting point is selected from the set P, the starting point is added to the set Q, the starting point is deleted from the set P, the distance from the starting point to a point adjacent to the starting point is added to the array N, and the distance from the starting point to a point not adjacent to the starting point is denoted by infinity.

In Operation 3, a point M whose distance to the set Q is smallest (that is, a point with the smallest edge weight among the untraversed points connected to all the traversed points) is selected, added to the set Q, and deleted from the set P.

In Operation 4, a point C adjacent to the point M is found, and whether the distance to the point C stored in the array N is less than the distance from the starting point through M to the point C is determined. If the distance to the point C stored in the array N is less than the distance from the starting point through M to the point C, the array N is updated. If the distance to the point C stored in the array N is not less than the distance from the starting point through M to the point C, a next point adjacent to the point M continues to be searched for, and Operation 4 is repeated until all the adjacent points of the point M are traversed.

The operations "a point M whose distance to the set Q is smallest (that is, a point with the smallest edge weight among the untraversed points connected to all the traversed points) is selected, added to the set Q, and deleted from the set P" and "a point C adjacent to the point M is found, and whether the distance to the point C stored in the array N is less than the distance from the starting point through M to the point C is determined. If the distance to the point C stored in the array N is less than the distance from the starting point through M to the point C, the array N is updated. If the distance to the point C stored in the array N is not less than the distance from the starting point through M to the point C, a next point adjacent to the point M continues to be searched for, and Operation 4 is repeated until all the adjacent points of the point M are traversed" are repeated until the traversal set P is empty, that is, the array N constitutes the pupil boundary in the polar coordinates.

FIG. 3 illustrates the process of changing the transformed pupil image (b) into the pupil image (c) with the boundary extracted in FIG. 3.

In the embodiment of the present disclosure, the found pupil boundary is converted from polar coordinates to Cartesian coordinates and corresponds to coordinates in the Cartesian coordinate system through the following calculation formula:

$$x = x_0 + r\cos\theta$$

$$y = y_0 + r\cos\theta.$$

The pupil contour in the Cartesian coordinate system in the pupil image (d) including a pupil contour in FIG. 3 is then expressed as the following formula:

$$S = \{x_i, y_i\}, i = 0, 1, 2, \dots, n.$$

In the above formula, n is the number of points within the contour.

In Operation 203, whether the two pupil contours are similar to a reference contour is determined.

In the embodiment of the present disclosure, the reference contour is a pupil contour extracted from a pupil reference image. The patient for whom the pupil reference image is acquired and the patient for whom the acquired two consecutive frames of pupil images are acquired are the same patient, the pupil reference image and the two consecutive frames of pupil images are all captured for the same eye of the patient, and the pupil reference image is a pupil image normally captured when the pupil of the same patient is not obscured.

In the embodiment of the present disclosure, the state of the eye can be determined through the similarity comparison between the pupil contour and the reference contour, thereby implementing better tracking. The similarity comparison is not affected by the size of the contour and is only related to the form of the contour. As a result, the size sudden changes of the pupil due to uneven incident light can be ignored.

In some embodiments, the reference contour in Operation 203 may be acquired through the following operations (Operations B1 to B4).

In Operation B1, a pupil reference image is acquired, where the pupil reference image is a reference image captured when a pupil is not obscured.

In Operation B2, polar coordinate transform is performed on the pupil reference image to obtain a transformed pupil reference image.

In Operation B3, a boundary of the pupil in the transformed pupil reference image is extracted based on a shortest path algorithm.

In Operation B4, inverse polar coordinate transform is performed on the boundary to obtain a reference contour of the pupil.

In the embodiments of the present disclosure, for the operations of extracting the reference contour of the pupil reference image which are consistent with the process of extracting the contour from one frame of pupil image in Operation 202, reference may be made to Operations A1 to A3 in Operation 202, and the details are not repeated here.

Figure 4:
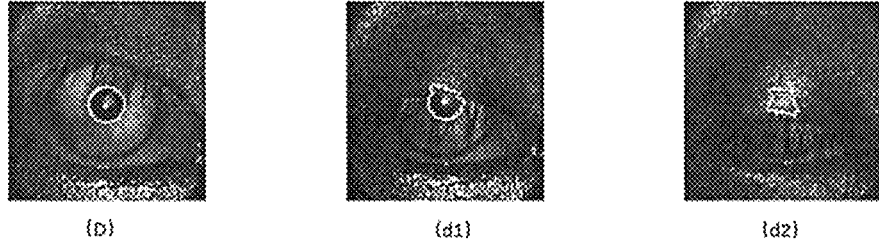
FIG. 4 is a schematic diagram in which a pupil contour is dissimilar to a reference contour according to an embodiment of the present disclosure.

FIG. 4 is a schematic diagram in which a pupil contour is dissimilar to the reference contour according to an embodiment of the present disclosure. With reference to FIG. 4, two pupil contours (d1) and (d2) are dissimilar to the reference contour in the pupil reference image (D). In other words, in the process of acquiring two consecutive frames of pupil images, a patient blinks his/her eyes or his pupil is obscured by the eyelid or eyelashes, that is, the pupil of the patient is obscured.

FIG. 5 is a schematic diagram in which a pupil contour is similar to the reference contour according to an embodiment of the present disclosure. With reference to FIG. 5, for one pupil image (d3), the pupil contour (d3) in the pupil image (d3) is similar to the reference contour in the pupil reference image (D). In other words, in the process of acquiring two consecutive frames of pupil images, a patient does not blink his/her eyes or the pupil is not obscured by his/her eyelids or eyelashes, that is, the pupil of the patient is not obscured. In this regard, if the distance between the reference contour in the pupil reference image (D) and the pupil contour in the pupil image is within a preset range, the pupil contour is determined to be similar to the reference contour, and it can be determined that the pupil of the patient is not obscured when the pupil image is acquired.

In some embodiments, Operation 203 includes Operations C1 to C2.

In Operation C1, the distance between the pupil contour and the reference contour is calculated.

In Operation C2, whether the pupil contour is similar to the reference contour is determined according to a preset distance range and the distance (that is, the distance calculation result obtained by performing Operation C1).

The distance between the pupil contour and the reference contour in the present disclosure is an image moment (Hu moment). The Hu moment of an image is an image feature with translation invariants, rotation invariants and scale invariants, and the Hu moment calculation includes ordinary moment calculation, central moment calculation and normalized central moment calculation.

In one embodiment, the distance between the pupil contour and the reference contour is calculated through normalized central moment calculation. The normalized central moment is a linear combination of normalized moments and can maintain invariance after operations such as image rotation, translation and scaling, and the normalized central moment is therefore often used for identifying the features of an image.

The distance between the pupil contour and the reference contour is calculated through the following formula:

$$D(A, B) = \sum_{i=0}^{6} \left| \frac{1}{m_i^B} - \frac{1}{m_i^A} \right|$$

where $m_i^A = \text{sign}(h_i^A) \cdot \log h_i^A$, and
$m_i^B = \text{sign}(h_i^B) \cdot \log h_i^B$.

In the above formula, A denotes the pupil contour, B denotes the reference contour, D(A, B) denotes the distance between the pupil contour and the reference contour, $$m_i^A \text{ and } m_i^B$$

denote the log-transformed Hu moments of the two contours, and $$h_i^A \text{ and } h_i^B$$

are the Hu moments of the contours A and B.

In the embodiment of the present disclosure, the distance between the pupil contour and the reference contour may also be calculated through the following formula:

$$D(A, B) = \sum_{i=0}^{6} \left| m_i^B - m_i^A \right|$$

where $m_i^A = \text{sign}(h_i^A) \cdot \log h_i^A$, and
$m_i^B = \text{sign}(h_i^B) \cdot \log h_i^B$.

In the above formula, A denotes the pupil contour, B denotes the reference contour, D(A, B) denotes the distance between the pupil contour and the reference contour, $$m_i^A \text{ and } m_i^B$$

denote the log-transformed Hu moments of the two contours, and $$h_i^A \text{ and } h_i^B$$

are the Hu moments of the contours A and B.

In the embodiment of the present disclosure, the preset distance range is a distance value range subjectively specified and can be set according to the requirements of the study. When the calculated distance is within the preset distance range, the pupil contour is similar to the reference contour.

In Operation 204, in response to the two pupil contours being similar to the reference contour, a central position offset of one of the two pupil contours with respect to the other pupil contour is calculated.

In the embodiment of the present disclosure, in the case where two pupil contours in two consecutive frames of pupil images are both similar to the reference contour, that is, in the case where the two consecutive frames of pupil images are normal, the central position offset of one of the two pupil contours with respect to the other pupil contour is calculated.

The central position offset of one pupil contour with respect to the other pupil contour is calculated through the following formulas:

$$\Delta x = x_B - x_A$$

$$\Delta y = y_B - y_A.$$

In the above formulas, $(x_A, y_A)$ and $(x_B, y_B)$ denote two pupil central positions, respectively, and $(\Delta x, \Delta y)$ denotes the central position offset of one pupil contour with respect to the other pupil contour.

In some embodiments, Operation 204 includes Operations D1 to D2.

In Operation D1, the center of mass of each pupil contour is acquired according to each pupil contour.

In Operation D2, the central position offset is calculated according to two centers of mass.

In the embodiment of the present disclosure, the pupil central position is acquired by calculating the center of mass of the contour.

In the embodiment of the present disclosure, the pupil central position (the center of mass of the contour) may be acquired by calculating points on the contour. With the method of acquiring the pupil central position $(x_A, y_A)$ as an example, the pupil central position is calculated by the following formulas:

$$x_A = \frac{1}{n}\sum_{i=1}^{n} x_i$$

$$y_A = \frac{1}{n}\sum_{i=1}^{n} y_i.$$

In the above formulas, $(x_A, y_A)$ denotes the coordinates of a pupil central position (that is, the center of mass of a pupil contour), and $(x_i, y_i)$ denotes the coordinates of an $i^{th}$ point on the contour.

In the embodiments of the present disclosure, by directly calculating the pupil central position instead of fitting the pupil central position using an ellipse fitting algorithm, errors introduced by the ellipse fitting algorithm itself in the case of using an ellipse fitting method can be avoided, and large errors caused when fitting is still performed with a preset shape (for example, an ellipse) in the case where the pupil of the patient may have been deformed can be avoided, thereby avoiding the resultant problem of inaccurate pupil identification.

In the embodiment of the present disclosure, Operations 201 to 204 are summarized below.

The capture method for acquiring the pupil images is continuous capturing. One pupil image is acquired in each capture, that is, the first pupil image in any one of the groups of two consecutive frames of pupil images in multiple frames of images is acquired. After contour extraction is performed on the first pupil image, the similarity comparison between the contour in the first pupil image and the reference contour is performed. If the contour in the first pupil image is similar to the reference contour, the capture continues, and the next pupil image is acquired, that is, the second pupil map in any one of the groups of two consecutive frames of pupil images in the multiple frames of images is acquired. After contour extraction is performed on the second pupil image, the similarity comparison between the contour in the second pupil image and the reference contour is performed. If the pupil contours corresponding to the two pupil images are similar to the reference contour, the two pupil images are determined to be valid, and the corresponding offset of the centers of the two pupil contours can be calculated.

In some embodiments, the method further includes Operation 205.

In Operation 205, in response to the two pupil contours being dissimilar to the reference contour, another two consecutive frames of pupil images are re-acquired, the contour extraction is performed on the two re-acquired consecutive frames of pupil images separately to obtain two pupil contours corresponding to the two re-acquired consecutive frames of pupil images, and whether the two pupil contours corresponding to the two re-acquired consecutive frames of pupil images are similar to the reference contour is determined, where the two re-acquired consecutive frames of pupil images are images adjacent to the two consecutive frames of pupil images acquired in Operation 201.

In an embodiment of the present disclosure, when two pupil contours are dissimilar to the reference contour, it is indicated that the patient blinks his/her eyes or his pupil is obscured by the eyelid or eyelashes, that is, the pupil of the patient is obscured. In the case where the pupil of the patient is obscured, the result subsequently obtained using an OCTA algorithm is inaccurate.

In an embodiment of the present disclosure, to acquire a more accurate OCTA image, two consecutive frames of pupil images adjacent to the two consecutive frames of pupil images acquired in Operation 201 are re-acquired, and the operation of separately performing contour extraction on the two re-acquired consecutive frames of pupil images to obtain two corresponding pupil contours and the operation of determining whether the two pupil contours are similar to the reference contour are performed until a more accurate OCTA image is acquired.

In an embodiment of the present disclosure, each subsequently captured image needs to be executed by using the above method according to the requirements of the study to improve the accuracy of the OCTA image.

Through the above schemes, in the eye tracking method for anterior segment OCTA provided in the embodiments of the present disclosure, two consecutive frames of pupil images are acquired, contour extraction is performed on the two frames of pupil images separately to obtain two corresponding pupil contours, the two pupil contours are compared with the reference contour, the pupil of the patient is determined not to be obscured during the acquisition of the two frames of pupil images if the two pupil contours are similar to the reference contour, and then the central position offset of one of the two pupil contours with respect to the other pupil contour is calculated and saved for the subsequent use in the OCTA algorithm, thereby obtaining a more accurate OCTA image. Therefore, the problems in the related art that OCTA is not suitable for all patients and especially the OCTA image is inaccurate when the patient has poor fixation, frequently blinks or moves eyeballs can be solved, the suitability for OCTA can be improved, and the pupil images captured in the case where the patient has poor fixation, frequently blinks or moves eyeballs can be excluded from being used, thereby achieving the effect of improving the accuracy of the OCTA image.

For the sake of simplicity, the above method embodiments are described as a series of action combinations. However, it is to be understood by those skilled in the art that the present disclosure is not limited by the described action sequence, because some operations may be performed in another sequence or concurrently according to the present disclosure. It is also to be understood by those skilled in the art that the embodiments described in the specification are optional embodiments and that the actions and modules involved may not be necessary for the present disclosure.

The above is the description of the method embodiments, and the schemes of the present disclosure will be described below through apparatus embodiments.

FIG. 6 is a structure diagram of an eye tracking apparatus for anterior segment OCTA according to an embodiment of the present disclosure. With reference to FIG. 6, the eye tracking apparatus for anterior segment OCTA includes an acquisition module 601, an extraction module 602, a determination module 603 and a calculation module 604.

The acquisition module 601 is configured to acquire two consecutive frames of pupil images. The extraction module 602 is configured to separately perform contour extraction on the two frames of pupil images to obtain two corresponding pupil contours. The determination module 603 is configured to determine whether the two pupil contours are similar to a reference contour. The calculation module 604 is configured to, in response to the two pupil contours being similar to the reference contour, calculate a central position offset of one of the two pupil contours with respect to the other pupil contour.

In some embodiments, the eye tracking apparatus for anterior segment OCTA further includes a re-acquisition module 605.

The re-acquisition module 605 is configured to, in response to the two pupil contours being dissimilar to the reference contour, re-acquire another two consecutive frames of pupil images, separately performing the contour extraction on the two re-acquired consecutive frames of pupil images to obtain two pupil contours corresponding to the two re-acquired consecutive frames of pupil images, and determining whether the two pupil contours corresponding to the two re-acquired consecutive frames of pupil images are similar to the reference contour; where the two re-acquired consecutive frames of pupil images are images adjacent to the two consecutive frames of pupil images acquired last time.

For the convenience and brevity of the description, the working process of the above-described modules, reference may be made to the corresponding process in the above method embodiments, and the details are not repeated here.

Figure 7:
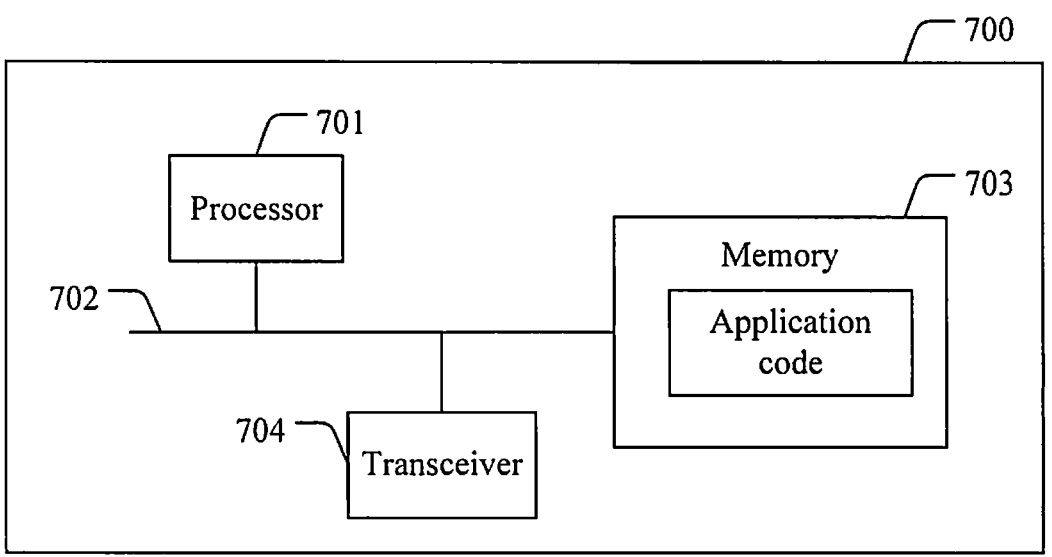
FIG. 7 is a structure diagram of an electronic device according to an embodiment of the present disclosure.

FIG. 7 is a structure diagram of an electronic device according to an embodiment of the present disclosure. As shown in FIG. 7, the electronic device 700 shown in FIG. 7 includes a processor 701 and a memory 703. The processor 701 and the memory 703 are connected to each other. In one embodiment, the electronic device 700 may further include a transceiver 704. In actual application, the number of the transceivers 704 is not limited to one, and the structure of the electronic device 700 does not constitute a limitation on the embodiments of the present disclosure.

The processor 701 may be a central processing unit (CPU), a general-purpose processor, a digital signal processor (DSP), an application-specific integrated circuit (ASIC), a field-programmable gate array (FPGA) or other programmable logic devices, transistor logic devices, hardware components, or any combination thereof. The processor may implement or execute a variety of example logic blocks, modules and circuits described in conjunction with the content of the present disclosure. The processor 701 may also be a combination that implements computing functions, such as a combination including one or more microprocessors or a combination of a DSP and a microprocessor.

A bus 702 may include a path for transmitting information between the foregoing components. The bus 702 may be a peripheral component interconnect (PCI) bus or an extended industry standard architecture (EISA) bus. The bus 702 may be divided into an address bus, a data bus, a control bus, and the like. For ease of representation, the bus 702 is represented by only one bold line in FIG. 7, but it does not mean that only one bus or one type of bus exists.

The memory 703 may be a read-only memory (ROM) or another type of static storage device that may store static information and instructions, a random-access memory (RAM) or another type of dynamic storage device that may store information and instructions, an electrically erasable programmable read-only memory (EEPROM), a compact disc read-only memory (CD-ROM) or other optical disc storage, optical disk storage (including compact disks, laser disks, optical disks, digital versatile disks and Blu-ray disks), a disk storage medium or another magnetic storage device, or any other media capable of carrying or storing desired program codes in the form of instructions or data structures and capable of being accessed by a computer, but not limited thereto.

The memory 703 is configured to store an application code for executing the scheme of the present disclosure, and the execution is controlled by the processor 701. The processor 701 is configured to execute the application program code stored in the memory 703 to implement the content illustrated in the above method embodiments.

The electronic device 700 includes, but is not limited to, a mobile terminal such as a mobile phone, a laptop, a digital broadcast receiver, a personal digital assistant (PDA), a portable Android device (PAD), a portable media player (PMP) and a car-mounted terminal (for example, a car-mounted navigation terminal), and a fixed terminal such as a digital television (TV) and a desktop computer. The electronic device 700 in FIG. 7 is merely an example and should not impose any limitation on the function and usage scope of the embodiments of the present disclosure.

An embodiment of the present disclosure provides a computer-readable storage medium. The computer-readable storage medium is configured to store a computer program which, when run on a computer, enables the computer to execute the corresponding content in the above method embodiments. With comparison with the related art, in the embodiments of the present disclosure, two consecutive frames of pupil images are acquired, contour extraction is performed on the two frames of pupil images separately to obtain two corresponding pupil contours, the two pupil contours are compared with the reference contour, the pupil of the patient is determined not to be obscured during the acquisition of the two frames of pupil images if the two pupil contours are similar to the reference contour, and then the central position offset of one of the two pupil contours with respect to the other pupil contour is calculated and saved for the subsequent use in the OCTA algorithm, thereby obtaining a more accurate OCTA image. Therefore, the problems in the related art that OCTA is not suitable for all patients and especially the OCTA image is inaccurate when the patient has poor fixation, frequently blinks or moves eyeballs can be solved, the suitability for OCTA can be improved, and the pupil images captured in the case where the patient has poor fixation, frequently blinks or moves eyeballs can be excluded from being used, thereby achieving the effect of improving the accuracy of the OCTA image.

Although the steps in the flowchart of the drawings are shown sequentially as indicated by the arrows, these steps are not necessarily executed sequentially in the order indicated by the arrows. Unless expressly stated here, the execution of these steps is not strictly limited in order, and these steps may be executed in another order. Moreover, at least part of the steps in the flowchart of the drawings may include multiple sub-steps or multiple phases. These sub-steps or phases are not necessarily executed at the same moment but may be executed at different moments, the order of execution thereof may not necessarily be performed sequentially, and these sub-steps or phases may be executed in turn or alternately with another step or at least part of the sub-steps or phases of another step.

What is claimed is:

1. An eye tracking method for anterior segment optical coherence tomography angiography (OCTA), comprising:

acquiring two consecutive frames of pupil images;

separately performing contour extraction on the two frames of pupil images to obtain two corresponding pupil contours;

determining whether the two pupil contours are similar to a reference contour; and in response to the two pupil contours being similar to the reference contour, calculating a central position offset of one of the two pupil contours with respect to the other pupil contour.

2. The method according to claim 1, wherein performing contour extraction on a frame of the two frames of pupil images comprises:

performing polar coordinate transform on the frame of pupil image to obtain a transformed pupil image;

extracting, based on a shortest path algorithm, a boundary of a pupil in the transformed pupil image; and performing inverse polar coordinate transform on the boundary to obtain a corresponding pupil contour.

3. The method according to claim 1, wherein determining whether a pupil contour of the two pupil contours is similar to the reference contour comprises:

calculating a distance between the pupil contour and the reference contour; and determining, according to a preset distance range and the distance, whether the pupil contour is similar to the reference contour.

4. The method according to claim 1, wherein the calculating a central position offset of one of the two pupil contours with respect to the other pupil contour comprises:

acquiring, according to each of the two pupil contours, a center of mass of each of the two pupil contours; and calculating, according to two centers of mass, the central position offset.

5. The method according to claim 1, further comprising:

in response to the two pupil contours being dissimilar to the reference contour, re-acquiring another two consecutive frames of pupil images, separately performing the contour extraction on the two re-acquired consecutive frames of pupil images to obtain two pupil contours corresponding to the two re-acquired consecutive frames of pupil images, and determining whether the two pupil contours corresponding to the two re-acquired consecutive frames of pupil images are similar to the reference contour;

wherein the two re-acquired frames of pupil images are images adjacent to the two consecutive frames of pupil images.

6. The method according to claim 1, wherein the reference contour is acquired through the following operations:

acquiring a pupil reference image, wherein the pupil reference image is a reference image captured when a pupil is not obscured;

performing polar coordinate transform on the pupil reference image to obtain a transformed pupil reference image;

extracting, based on a shortest path algorithm, a boundary of the pupil in the transformed pupil reference image; and performing inverse polar coordinate transform on the boundary to obtain a reference contour of the pupil.

7. An electronic device, comprising a memory and a processor, wherein the memory is configured to store a computer program, and the processor is configured to, when executing the computer program, implement the following steps:

acquiring two consecutive frames of pupil images;

separately performing contour extraction on the two frames of pupil images to obtain two corresponding pupil contours;

determining whether the two pupil contours are similar to a reference contour; and in response to the two pupil contours being similar to the reference contour, calculating a central position offset of one of the two pupil contours with respect to the other pupil contour.

8. A non-transitory computer-readable storage medium storing a computer program, wherein the computer program, when executed by a processor, causes the processor to implement the following steps:

acquiring two consecutive frames of pupil images;

separately performing contour extraction on the two frames of pupil images to obtain two corresponding pupil contours;

determining whether the two pupil contours are similar to a reference contour; and in response to the two pupil contours being similar to the reference contour, calculating a central position offset of one of the two pupil contours with respect to the other pupil contour.

9. The device according to claim 7, wherein performing contour extraction on a frame of the two frames of pupil images comprises:

performing polar coordinate transform on the frame of pupil image to obtain a transformed pupil image;

extracting, based on a shortest path algorithm, a boundary of a pupil in the transformed pupil image; and performing inverse polar coordinate transform on the boundary to obtain a corresponding pupil contour.

10. The device according to claim 7, wherein determining whether a pupil contour of the two pupil contours is similar to the reference contour comprises:

calculating a distance between the pupil contour and the reference contour; and determining, according to a preset distance range and the distance, whether the pupil contour is similar to the reference contour.

11. The device according to claim 7, wherein the calculating a central position offset of one of the two pupil contours with respect to the other pupil contour comprises:

acquiring, according to each of the two pupil contours, a center of mass of each of the two pupil contours; and calculating, according to two centers of mass, the central position offset.

12. The device according to claim 7, wherein the processor is further configured to, when executing the computer program, implement the following steps:

in response to the two pupil contours being dissimilar to the reference contour, re-acquiring another two consecutive frames of pupil images, separately performing the contour extraction on the two re-acquired consecutive frames of pupil images to obtain two pupil contours corresponding to the two re-acquired consecutive frames of pupil images, and determining whether the two pupil contours corresponding to the two re-acquired consecutive frames of pupil images are similar to the reference contour;

wherein the two re-acquired frames of pupil images are images adjacent to the two consecutive frames of pupil images.

13. The device according to claim 7, wherein the reference contour is acquired through the following operations:

acquiring a pupil reference image, wherein the pupil reference image is a reference image captured when a pupil is not obscured;

performing polar coordinate transform on the pupil reference image to obtain a transformed pupil reference image;

extracting, based on a shortest path algorithm, a boundary of the pupil in the transformed pupil reference image; and performing inverse polar coordinate transform on the boundary to obtain a reference contour of the pupil.

14. The storage medium according to claim 8, wherein performing contour extraction on a frame of the two frames of pupil images comprises:

performing polar coordinate transform on the frame of pupil image to obtain a transformed pupil image;

extracting, based on a shortest path algorithm, a boundary of a pupil in the transformed pupil image; and performing inverse polar coordinate transform on the boundary to obtain a corresponding pupil contour.

15. The storage medium according to claim 8, wherein determining whether a pupil contour of the two pupil contours is similar to the reference contour comprises:

calculating a distance between the pupil contour and the reference contour; and determining, according to a preset distance range and the distance, whether the pupil contour is similar to the reference contour.

16. The storage medium according to claim 8, wherein the calculating a central position offset of one of the two pupil contours with respect to the other pupil contour comprises:

acquiring, according to each of the two pupil contours, a center of mass of each of the two pupil contours; and calculating, according to two centers of mass, the central position offset.

17. The storage medium according to claim 8, wherein the computer program, when executed by the processor, further causes the processor to implement the following steps:

in response to the two pupil contours being dissimilar to the reference contour, re-acquiring another two consecutive frames of pupil images, separately performing the contour extraction on the two re-acquired consecutive frames of pupil images to obtain two pupil contours corresponding to the two re-acquired consecutive frames of pupil images, and determining whether the two pupil contours corresponding to the two re-acquired consecutive frames of pupil images are similar to the reference contour;

wherein the two re-acquired frames of pupil images are images adjacent to the two consecutive frames of pupil images.

18. The storage medium according to claim 8, wherein the reference contour is acquired through the following operations:

acquiring a pupil reference image, wherein the pupil reference image is a reference image captured when a pupil is not obscured;

performing polar coordinate transform on the pupil reference image to obtain a transformed pupil reference image;

extracting, based on a shortest path algorithm, a boundary of the pupil in the transformed pupil reference image; and performing inverse polar coordinate transform on the boundary to obtain a reference contour of the pupil.

* * * * *